(12) United States Patent
Shigeta et al.

(10) Patent No.: US 6,565,890 B2
(45) Date of Patent: May 20, 2003

(54) ANTIVIRAL DRUGS CONTAINING HETEROPOLYANIONS

(75) Inventors: Shiro Shigeta, Fukushima (JP); Toshihiro Yamase, Kanagawa (JP)

(73) Assignee: Polytronics, Ltd., Ishikawa-ken (JP)

( * ) Notice: Subject to any disclaimer, the term of this patent is extended or adjusted under 35 U.S.C. 154(b) by 0 days.

(21) Appl. No.: 09/934,751

(22) Filed: Aug. 22, 2001

(65) Prior Publication Data

US 2003/0039702 A1 Feb. 27, 2003

(51) Int. Cl.[7] .................. A01N 59/00; A61K 33/00
(52) U.S. Cl. .................. 424/600; 514/885; 514/888
(58) Field of Search .................. 424/600; 514/888, 514/885

(56) References Cited

FOREIGN PATENT DOCUMENTS

JP          2000-229864        8/2000

OTHER PUBLICATIONS

Yamase et al., Chemical and Intramolecular Spin–Exchange Interaction of [(VO)3(SbW9O33)2]12–, Oct. 10, 2000, Chemistry Letters, pp. 56–57.*

Botar et al., Synthesis and crystal structure of a novel vanadium–containing tungstobismutate(III) K12 [(VO)3(BiW9O33)2]30H2O), Jun. 11, 2001, Elsevier Science S.A., 4(10), pp. 551–554.*

* cited by examiner

*Primary Examiner*—Jose' G. Dees
*Assistant Examiner*—Konata M. George
(74) *Attorney, Agent, or Firm*—Frishauf, Holtz, Goodman & Chick, P.C.

(57) ABSTRACT

A compound for use especially as an antiviral drug, mainly containing salts of heteropolyanions consisting of a tungstoantimonate (III) vanadium-mixed metal oxide or related salts represented by formula $[(XW_9O_{33})_2V_3O_3]^{P-}$, where p is a positive number between 9 and 12 and X is Sb, P, As or Bi and especially Sb. An antiviral drug having a broad spectrum of antiviral activity, high potent efficacy and low toxicity is provided.

12 Claims, 3 Drawing Sheets

FIG.1 $[(SbW_9O_{33})_2V_3O_3]^{p-}$ $9 \leq p \leq 12$

FIG.2

ANTI-HIV EFFECT AND CYTOTOXICITY OF HETEROPOLYANIONS AND OTHER DRUGS

| CELL | DRUG | $EC_{50}$ | $EC_{90}$ | $CC_{50}$ | SI |
|---|---|---|---|---|---|
| | | | $\mu m$ | | |
| MT-4 | PM-1001 | 0.138±0.067 | ND | 41.9±2.88 | 304 |
| | PM-1002 | 0.0300±0.010 | ND | 45.9±0.29 | 1530 |
| | PM-1003 | >6.22 | ND | 6.22±2.63 | |
| | DS5000 | 0.652±0286 | | >20 | >30.7 |
| HeLa CD4 | PM-1001 | 0.0096±0.0056 | 0.11±0.057 | >100 | >10417 |
| | PM-1002 | 0.0177±0.0071 | 0.112±0.054 | >100 | >5650 |
| | DS5000 | 0.0059±0.0018 | 0.127±0.055 | >20 | >3390 |
| | AZT | 0.037±0.023 | 0.416±0.327 | >100 | >2703 |

FIG. 3

ANTIVIRAL EFFECT OF HETEROPOLYANIONS AND RIBAVIRIN : $EC_{50}$ (iM)

| DRUG | anti-DFV | anti-FluV-A | anti-RSV | anti-PfluV-2 | anti-COV | anti-HIV-1 | anti-HSV-1 |
|---|---|---|---|---|---|---|---|
| PM-43 | 10.7±6.7 | 8.4±6.5 | 1.6± | >100 | 7.5±0.95 | 0.3±0.12 | NT |
| PM-47 | 10.5±6.9 | 11.5±0.6 | 29±15.7 | 67.1±32.9 | 6.0±0.59 | 0.03±0.01 | NT |
| PM-518 | 36.8±9.5 | 62.3±26.5 | 25.6±8.1 | 53.2±39.2 | >50 | 2.0±0.8 | NT |
| PM-520 | 11.1±7.1 | 45.2±25.8 | 0.74±0.58 | 3.2±2.4 | 7.4±0.39 | 2.0±0.5 | NT |
| PM-523 | >61.5 | 6.5±3.7 | 1.27±0.46 | 2.5±1.0 | 7.3±1.12 | 0.3±0.07 | NT |
| PM-1001 | 0.45±0.35 | 5.3±0.7 | <0.16 | 1.1±0.9 | | 0.14±0.07 | 1.62 |
| PM-1002 | 1.97±1.42 | 4.6±1.7 | 0.75±0.05 | 0.75±0.05 | | 0.03±0.01 | 0.3 |
| Ribavirin | >100 | 9.6±2.6 | 3.9±3.1 | 14.0±4.8 | 73.6±34.5 | NT | NT |

PM-43 ; $K_5[SiVW_{11}O_{40}]$

PM-47 ; $K_7[BVW_{11}O_{40}]$

PM-518 ; $[Et_2NH_2]_7[PTi_2W_{10}O_{40}]$

PM-520 ; $[Pri_2NH_2]_5[PTiW_{11}O_{40}]$

PM-523 ; $[PriNH_3]_6H[PTi_2W_{10}O_{38}(O_2)_2]H_2O$

ANTIVIRAL DRUGS CONTAINING HETEROPOLYANIONS

This application is based on Japanese patent application HEI 11-30342, filed on Feb. 8, 1999, and published as JP-A 2000-229864 on Aug. 22, 2000, the whole contents of which are incorporated herein by reference.

BACKGROUND OF THE INVENTION

1. Field of the Invention

The present invention relates to a novel antiviral drug containing heteropolyanions of inorganic metal oxides as an active ingredient; and to its use as an antiviral drug.

2. Description of the Related Art

There are a wide variety of viruses that infectiously affect vital bodies for causing various diseases. Against some viruses, highly potent vaccines are developed, but against such viruses as influenza viruses, the vaccines developed for them are low in potency since there exist too many kinds of viruses to be covered by vaccination. Furthermore, in the case of the viruses that cause acute infection for trapping patients into severe conditions, chemotherapies are said to be necessary. The viral infections that are considered to require chemotherapies include infections mainly causing respiratory diseases without any vaccine available (RS virus, influenza virus, etc.), infections that are reactivated and plunge patients into severe conditions under immunosuppressed conditions (herpes simplex virus, cytomegalovirus, etc.), infections that become chronic and keep patients in a carrier state (hepatitis B and C viruses, HIV, etc.), infections of viruses causing vertical infection (rubella virus, varicella-zoster virus, etc.), and infections of hemorrhagic fever viruses such as Ebola hemorrhagic fever. To control these infections respectively, R&D is being conducted on antiviral drugs, but except those having limited effects, no antiviral drug having a broad spectrum of antiviral activity and having little adverse effect has been actually utilized.

Each antiviral drug is developed to target any stage of infection, growth and desorption of the virus concerned. For example, one of inhibitors in the infection stage (adsorption, entering and uncoating of the virus) is dextran sulfate effective against HIV (human immunodeficiency virus), RSV (RS virus), Fluv-A (influenza virus A), etc. Furthermore, inhibitors in the growth stage (replication and transcription of nucleic acid, synthesis and processing of protein and virion formation) include acyclovir effective against HSV (herpes simplex virus), VZV (varicella-zoster virus), etc., AZT (azidothymidine) effective against HIV, ribavirin inhibiting the replication of RNA of various RNA viruses, etc. Inhibitors in the desorption stage (release of virus particles and syncitium formation) include bicyclam effective against HIV and RSV.

However, these conventional antiviral drugs are not always sufficiently high in the antiviral effect or sufficiently low in adverse effects, and also have a problem that resistant strains are likely to be formed. Most of these antiviral drugs are organic compounds. Therefore, for future development of antiviral drugs, it is important to select drugs from a viewpoint different from the conventional one.

SUMMARY OF THE INVENTION

An object of this invention is to provide a novel antiviral drug having an spectrum of antiviral activity broader and an antiviral effect stronger than those of the antiviral drugs developed so far such as ribavirin, DS (dextran sulfate) and AZT (azidothymidine) and having a very low adverse effect.

Another object of this invention is to disclose new polyoxometalate anions having a molecular structure quite different from those of inorganic compounds reported to have antiviral effects, i.e., polyoxotungstate salts such as 21-tungsto-9-antimonate (HPA-23), heteropolyanion 5-tungsto-2-antimonate and ammonium 5-tungsto-2-antimonate, and also having both an incomparably strong antiviral effect and low adverse effect.

An aspect of this invention uses an antiviral drug containing alkaline metal salts of heteropolyanions composed of tungstoantimonate (III) (this (III) means trivalent antimony) vanadium-mixed metal oxide ions represented by general formula $[(SbW_9O_{33})_2V_3O_3]^{p-}$ (where p is a positive number between 9 to 12). The alkaline ions for forming the salts with the heteropolyanions include alkali metal ions, alkaline earth metal ions, organic or inorganic ammonium ions, and hydride metal (or ammonium) ions. These alkali metal salts may have 50 molecules or less of crystal water. Said antiviral drug mainly composed of the alkaline metal salts is usually provided as a solid or liquid having 0.1 to several mol percent of them dispersed in a matrix, and it is administered into living bodies by any adequate method selected from peroral method, permucosal method, percutaneous method or injection.

It has been demonstrated that the above-mentioned drug as a novel chemical substance is an ideal antiviral drug having a spectrum of antiviral activity broader than those of many known antiviral drugs, and exhibiting a higher potent efficacy and low toxicity. The salt of the heteropolyanion may include cations of various kinds. Of course, when used as a drug, treatment, e.g. of humans, the salt must include pharmaceutically acceptable cations. The compound may be made soluble or insoluble in water as desired depending in part on the cation selected and can be provided as part of various formulations such as tablets and injection drug. Furthermore, the drug is stable also as a preparation. The tungstoantimonate (III) vanadium-mixed metal oxide ions as the main active ingredient of the drug also have an advantage that the molecule can be designed to give the most suitable effect against numerous RNA and DNA viruses, depending on the kind of the alkali ions used for forming the salts and the number of hydrogen ions. With the above effects, the drug exhibits very excellent properties as an antiviral drug.

BRIEF DESCRIPTION OF THE DRAWINGS

FIG. 2 is a data list.

FIG. 3 is another data list.

DESCRIPTION OF THE PREFERRED EMBODIMENTS

Figure 1:
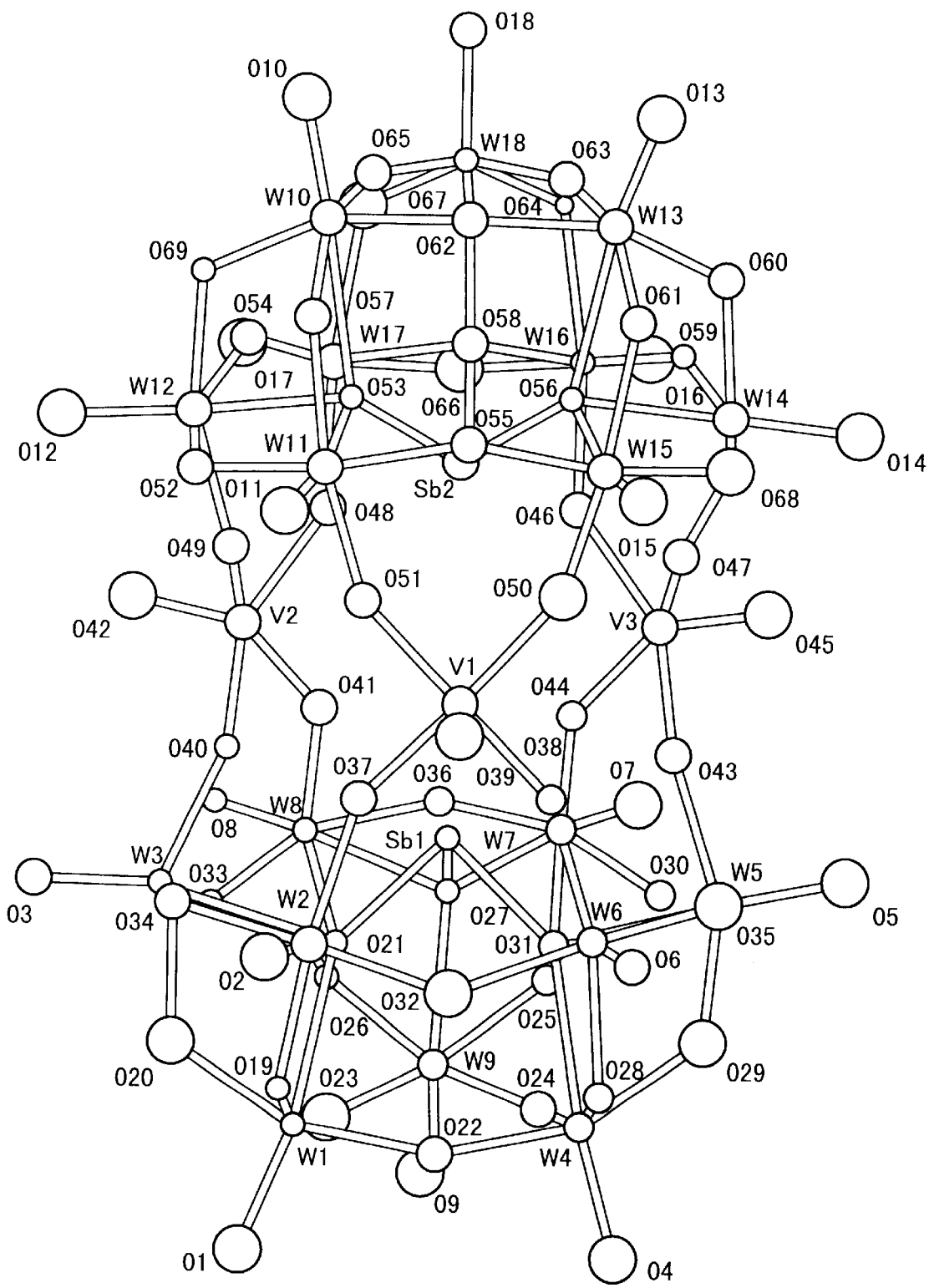
FIG. 1 is a model diagram showing the molecular structure of $[SbW_9O_{33})_2V_3O_3]^{p-}$ as the framework of the molecule of this invention.

The general structure of the heteropolyanions used in this embodiment is shown in FIG. 1. As illustrated, it has a specific structure, in which two sets of polyoxotungstate ions having Sb ions as heteroions at the center are symmetrically combined with each other via vanadate ions, and it is called deficient Keggin-sandwich-typed polyanions. The valence of anions is 9 to 12, and it depends on the valences of the alkali and hydrogen ions constituting the salts. For the metal elements constituting the polyanions, respectively three to six oxygen atoms are coordinated to form units, and they are combined via ridges or vertexes to structurally form an polyoxometalate complex.

The antiviral drug of this invention has a feature, in which usually a solid or liquid carrier (matrix), preferably a liquid carrier contains at least one of the salts of the heteropolyanions, and it can also be used with a help of a known bioactive compound.

This drug is described below in more detail in reference to examples.

SYNTHESIS EXAMPLE (1)

1.96 g of $Sb_2O_3$ (6.7 millimole in concentration) was dissolved into 10 ml of 6N hydrochloric acid aqueous solution. Then, 40 g of $Na_9WO_4$ (120 millimoles in concentration) was dissolved into 80 ml of water, and the solution was boiled. To it, said hydrochloric acid aqueous solution was added, and the mixture was kept at 80 to 90° C. for about 1 hour. In this case, the pH of the aqueous solution was 7.0 to 7.5. It was cooled to room temperature, and the obtained crystal was washed with water and dried. The structure of it was X-ray-analyzed, and the crystal was confirmed to be $Na_9[SbW_9O_{33}]$.

SYNTHESIS EXAMPLE (2)

4.1 g of sodium acetate ($CH_3COONa$) and 3 ml of acetic acid ($CH_3COOH$) were dissolved into 50 ml of water, to make a buffer solution, and 1.5 g of finely ground sodium vanadate ($NaVO_3$) was added to the solution. Then, 10.6 g of $Na_9[SbW_9O_{33}]$ obtained in the above (1) was added to the solution, and the mixture was gradually heated. The color of the solution gradually changed from yellowish brown to black with temperature rise. After heating to 60° C., the solution was kept for 1 hour and filtered. To the filtrate, 10 to 12 g of KCl was added, and a brown precipitate was obtained. The precipitate was added to 70 to 80 ml of hot water, and the mixture was allowed to stand for about 1 day, to obtain a black crystal. The crystal was washed with water and dried, and the structure of it was analyzed by various analyzing means including X-ray analysis. The crystal was found to be $K_6H_4[(SbW_9O_{33})_2V_3O_3]\cdot 29.5H_2O$. The heteropolyoxometalate salts are called PM-1001.

SYNTHESIS EXAMPLE (3)

7 g of sodium acetate ($CH_3COONa$) and 1.5 ml of acetic acid ($CH_3COOH$) were dissolved into 50 ml of water, to make a buffer solution, and with it, an aqueous solution obtained by dissolving 2 to 3 g of vanadyl sulfate ($VOSO_4\cdot 5H_2O$) into 60 ml of water was mixed. To the mixed solution, 8 g of $Na_9[SbW_9O_{33}]$ was added, when the color of the solution changed from blue to reddish brown. The solution was kept at 40 to 60° C. for 1 hour and filtered. To the filtrate, 10 g of KCl was added, to obtain a precipitate. The precipitate was separated, and added to 70 to 80 ml of hot water. The mixture was allowed to stand. Two to three hours later, a reddish brown re-crystal was obtained. The structure of the crystal was analyzed using various physical analyzing means including X-ray analysis, and it was found to be $K_6H_6[(SbW_9O_{33})_2V_3O_3]\cdot 29.5H_2O$. The heteropolyoxometalate salts are called PM-1002. In PM-1002, vanadium ions were hexavalent, unlike pentavalent ions in PM-1001.

EXAMPLE

The antiviral effect against HIV (human immunodeficiency virus) and cytotoxicity of the PM-1001 and PM-1002 of this invention synthesized as described above were examined in comparison with those of $K_6[C_0W_{12}O_{40}]$. (called PM-1003), i.e., a heteropolyoxotungstate salt having perfect Keggin structure and conventional dextran sulfate (DS5000) and azidothymidine (AZT) respectively utilized because of their excellent anti-HIV effect. The inhibition of cell growth of HIV was measured according to the MTT colorimetric method.

The tissue culture cells were MT-4 and Hela CD4. The HIV was prepared from the supernatant solutions of the culture fluids of HIV-producing MT-4 and HIV cells, or Hela CD4 and HIV cells. The media were 10% fetal calf serum, and for culturing, 0.2 ml of MT-4 cells or Hela CD4 cells and 0.2 ml of HIV cells were placed in each well of a 24-well culture tray. After virus adsorption (the virus infectivity titer was 100-CCID50 per about $10^5$ cells), each drug such as PM-1001 diluted in a medium was added, to make a total amount of 1.0 ml, and the mixture was cultured at 37° C. for 4 to 6 days. As controls, cells not infected with HIV and cells untreated with any drug such as PM-1001 were used. After completion of culture, the respective vital cell numbers in the virus-infected cells and non-infected cells were examined by means of MTT dyeing and colorimetry. MTT is an abbreviation of 3-(4,5-dimethylthioazole-2-Y)-2,5-diphenyltetrazolium bromide. If cells are dyed with MTT, vital cells take it up inwardly and are reduced to emit reddish violet color. This phenomenon is used for the colorimetry. In the MTT colorimetry, the absorbance is measured by means of a colorimeter using a wavelength of 540 nm, to obtain the vital cell number proportional to the absorbance. If all the cells are dead due to virus infection, the absorbance becomes almost zero.

With the concentration of each drug such as PM-1001 as a parameter, the cell growth rate was examined. As a result, the data of FIG. 2 were obtained. In FIG. 2, $EC_{50}$ means the drug concentration ($\mu$m) at which the cytocidal (cycopathic) cell degeneration caused by HIV can be inhibited by 50%. That is, the drug concentration capable of improving the absorbance of virus-non-infected cells up to 50% (to prevent cytocidal cell degeneration) is obtained and expressed in micromoles ($\mu$M). If $EC_{50}$ is low, the drug has a corresponding high effect. Furthermore, $EC_{90}$ is the drug concentration ($\mu$M) at which the cytopathic cell degeneration by HIV can be inhibited by 90%, and $CC_{50}$ is the amount of a drug at which 50% of cells become dead (50% cytocidal concentration, $\mu$M). SI is called a chemotherapeutic index, being the titer obtained by dividing the toxic concentration by the effective concentration, i.e., $CC_{50}/EC_{50}$ in this case. If the index value is higher, the adverse effect is lower and the potent efficacy of the drug is higher. ND stands for "not determined".

FIG. 2 shows that the PM-1001 and PM-1002 of this invention exhibit very high potent efficacies and low adverse effects against the HIV produced with either MT-4 cells or Hela CD4 cells. These efficacies are sufficiently exhibited even in comparison with the DS5000 and AZT used hitherto as anti-HIV agents and the PM-1003 having a Keggin structure belonging to heteropolyanions, to clearly suggest that the heteropolyanion drug of this invention has excellent selective activity for anti-HIV. Especially as typically shown by the Hela CD4 cell line, it is noteworthy that the drug of this invention is lower in cytotoxicity and higher in the safety for vital bodies than existing anti-HIV agents.

The drug of this invention shows excellent inhibition of cell growth against not only HIV but also other viruses and has a broad spectrum of antiviral activity. In general, it is known that polyoxometalate anion compounds have broad spectra of antiviral activity, and it is reported that various heteropolyanions as described before such as HPA-23 have antiviral activity. The present inventors also developed drugs exhibiting antiviral activity using various heteropolyoxometalates different in crystal structure (for example, Kagaku Kogyo (=Chemical Industry), Vol. 41, pages 40–47, October 1990 issue). These heteropolyanions developed by the inventors exhibit antiviral activity higher than the known conventional polyanions such as HPA-23, but the drug of this invention has an antiviral effect far stronger than the effects of those heteropolyanions.

FIG. 3 compares: the PM-1001 and 1002 of the present invention with other heteropolyanions developed before by the present inventors in potent efficacy. This list shows what effective physiological activity the respective polyoxotungstate salts exhibit against respective viruses in reference to $EC_{50}$ ($\mu M$). In the list, NT stands for "Not tested". For comparison, the list also shows the data of a known antiviral drug, ribavirin said to show a broad spectrum of antiviral activity against RNA viruses (corresponding to DFV, FluV, PfluV, CDV and HIV in FIG. 3). DFV refers to dengue virus; FluV, influenza virus; RSV, RS virus (one of pathological viruses of respiratory infections); PfluV, Parainfluenza virus; CDV, distemper virus; and HIV, herpes simplex virus. The drug concentrations of $EC_{50}$ were measured according to said MTT colorimetric method. In this case, the tissue culture cells used for DFV were CV-1 cells (derived from monkey kidney); those for FluV-A, MDCK cells (derived from canine kidney); those for RSV, $HE_{p-2}$ cells (derived from human epiglottis carcinoma); those fort PfluV, HMV-2 cells (derived from human melanoma); those for CDV, Vero cells (derived from monkey kidney); those for HIV, MT-4 cells (derived from human T-lymphocytes); and those for HSV, RPM18226 cells (derived from human B-lymphocytes).

FIG. 3 clearly shows that the many heteropolyoxotunstate ions developed before by the present inventors exhibit antiviral effects almost equivalent to that of presently utilized ribavirin, and that the drugs (PM-1001 and PM-1002) of this invention exhibit remarkably excellent antiviral effects. The heteropolaynions of this invention exhibit high potent efficacies against all the RNA viruses tested, and also exhibit a strong potent efficacy even against a DNA virus, HSV-1. Though not shown in FIG. 3, the toxicity $CC_{50}$ values of the respective drugs for respective culture cells were examined, and the drugs of this invention and ribavirin were more than 100 $\mu M$.

The mechanism of antiviral activity of the drug of this invention is not clear, but since the drug has potent efficacies against not only RNA viruses but also DNA viruses and exhibits low effects in the early stage of drug administration (0 to 1.5 hours), it is considered that it inhibits the adsorption of viruses and prevents them from entering into the cells, also acting to inhibit the release of virus particles. To examine acute toxicity, PM-1001 and PM-1002 were respectively dissolved as aqueous solutions which were administered into the abdominal cavities of ICR/CD-1 dominant mice. Even when 500 mg/kg was administered, the decrease in body weight and other toxicity were not exhibited. That is, the drug of this invention is not only very low in cytotoxicity in vitro but also very low in the toxicity to mice.

The above example describes the potent efficacies and adverse effects of PM-1001 and PM-1002 drugs, but this invention is not limited to these compounds. It was confirmed that alkylammonium salts and magnesium compounds of $[(SbW_9O_{33})_2V_3O_3]^{p-}$ had similarly high potent efficacies and safety. It was also found that, the heteropolytungsten vanadate ions obtained by substituting the hetero atom Sb in the drugs for Bi exhibited similar effects. It is expected that those salts obtained by substituting Sb for other group V element, P or As respectively will also exhibit similar effects.

Any suitable dosage may be given in the method of the invention as can be estimated from the relative activity of the present invention antiviral agents to known antiviral agents. The type of compound carrier, the manner of administration and the amount can easily be determined by persons working with this type of drug, and will vary widely depending on the species of the warm blooded animal or human, body weight, and severity of viral infection being treated. Generally a dosage of between about 1 milligram (mg) per kilogram (kg) of body weight and about 800 mg per kg of body weight is suitable. Preferably from 5 mg to about 500 mg/kg and most preferably from about 10 mg/kg to about 100 mg/kg of body weight is used. A dosage unit may comprise a single compound or mixtures thereof with other compounds or other antiviral agents. The dosage unit can also comprise diluents, extenders, carriers and the like. The unit may be in solid or gel form such as pills, tablets, capsules and the like or in liquid form suitable for administration.

The above is intended to be illustrative but not limitative of the invention.

What is claimed is:

1. An antiviral drug containing an effective amount of a mixed metal oxide salt of heteropolyanions of the following formula $[(XW_9O_{33})_2V_3O_3]^{9-}$ where p is a positive number between 9 and 12 and X is Sb, P, As or Bi in a pharmaceutically acceptable carrier.

2. The antiviral drug of claim 1 wherein the salt is a salt of heteropolyanions consisting of a tungstoantimonate (III) vanadium-mixed metal oxide represented by $[(SbW_9O_{33})_2V_3O_3]^{p-}$, where p is a positive number between 9 and 12.

3. The antiviral drug of claim 2, wherein the salt includes at least one cation selected from the group consisting of alkali metal ions, alkaline earth metal ions, ammonium ions, and hydride metal ions.

4. The antiviral drug according to claim 1, wherein the pharmaceutically acceptable carrier is a solid on liquid matrix.

5. The antiviral drug according to claim 1, wherein the salt has a chemical formula of $K_6H_4[(SbW_9O_{33})_2V_3O_3] \cdot 29.5H_2O$.

6. The antiviral drug according to claim 1, wherein the salt has a chemical formula of $K_6H_6[(SbW_9O_{33})_2V_3O_3] \cdot 29.5H_2O$.

7. A method of treating a viral infection comprising administering to a patient in need thereof, an antivirally effective amount of the antiviral drug of claim 1.

8. A method of treating a viral infection comprising administering to a patient in need thereof, an antivirally effective amount of the antiviral drug of claim 5.

9. A method of treating a viral infection comprising administering to a patient in need thereof, an antivirally effective amount of the antiviral drug of claim 6.

10. The method of claim 7 wherein the viral infection is caused by RS virus, influenza virus, herpes simplex virus, cytomegolovirus, hepatitis B and C viruses, HIV, Rubella virus, varicella-zoster virus and hemorrhagic fever viruses.

11. A method of inhibiting RNA viruses in a patient comprising administering to a patient in need thereof, an effective amount of a mixed metal oxide salt of heteropolyanions of the following formula $[(XW_9O_{33})_2V_3O_3]^{9-}$ where p is a positive number between 9 and 12 and X is Sb, P, As or Bi.

12. A method of inhibiting DNA viruses in a patient comprising administering to a patient in need thereof, an effective amount of a mixed metal oxide salt of heteropolyanions of the following formula $[(XW_9O_{33})_2V_3O_3]^{9-}$ where p is a positive number between 9 and 12 and X is Sb, P, As or Bi.

* * * * *